United States Patent
Krylov et al.

(10) Patent No.: US 8,476,314 B2
(45) Date of Patent: Jul. 2, 2013

(54) SUBSTANCE WITH SEDATIVE EFFECT

(75) Inventors: Boris Vladimirovich Krylov, St.-Petersburg (RU); Ilya Vyacheslavovich Rogachevsky, St. Petersburg (RU); Vera Borisovna Plakhova, St. Petersburg (RU)

(73) Assignee: Technology Commercialization Corp, Chester, VT (US)

( * ) Notice: Subject to any disclaimer, the term of this patent is extended or adjusted under 35 U.S.C. 154(b) by 0 days.

(21) Appl. No.: 13/225,328

(22) Filed: Sep. 2, 2011

(65) Prior Publication Data

US 2012/0232136 A1 Sep. 13, 2012

Related U.S. Application Data (63) Continuation of application No. 11/459,659, filed on Jul. 25, 2006, now abandoned, and a continuation-in-part of application No. 10/389,538, filed on Mar. 14, 2003, now Pat. No. 7,087,640.

(30) Foreign Application Priority Data

Mar. 19, 2002 (RU) .................................. 2002107079

(51) Int. Cl.
*A01N 43/16* (2006.01)

(52) U.S. Cl.
USPC ............................ 514/460; 514/451; 424/400

(58) Field of Classification Search
None
See application file for complete search history.

(56) References Cited

U.S. PATENT DOCUMENTS

| | | | | |
|---|---|---|---|---|
| 5,998,397 A | * | 12/1999 | Bernstein ...................... | 514/184 |
| 6,228,347 B1 | * | 5/2001 | Hersh ............................ | 424/49 |
| 2003/0069218 A1 | * | 4/2003 | Stockham et al. ............ | 514/184 |

OTHER PUBLICATIONS

Khrapov et al. Bull Exp Bio Med 1 1998, translated from Byulleten' Eksperimental'noi Biologii i Meditsiny 125(1), 63-65, Jan 1998.*
Hwang and Yaksh, Pain 70, 15-22, 1997.*
Lipman and Blumenkopf pain 39, 249-256, 1989.*
CAPLUS abstract accesion No. 2000:909760 Shurygin et al. Izvestiya Vysshikh Uchebnykh Zavedenii (2000), 1, p. 100-101.*
Balisum-2 Instructions for Use, Registration No. 85/129/2 (in Russian), 2006.
I. V. Rogachevsky, V. B. Plakhova, S. A. Podzorova. Metal-bound forms of 4H-pyran-4-one derivatives modulate nociceptive responses of sensory neurons. Abstract for Alexander von Humboldt Foundation Conference titled "Technologies of the 21st century: biological, physical, informational and social aspects", Saint-Petersburg, Russia, Sep. 27-29, 2005.
I. V. Rogachevsky, V. B. Plakhova. Quantum-Chemical Study of the Equilibrium Geometry and Electronic Structure of Certain Gamma-Pyrone Derivatives. Russian Journal of general chemistry. 76;11:1820-1833, 2006.

* cited by examiner

*Primary Examiner* — Nissa Westerberg
(74) *Attorney, Agent, or Firm* — Boris Leschinsky (57) ABSTRACT

A substance with sedative effect comprises a therapeutically effective amount of a gamma-pyrone such as comenic acid in a pharmaceutically acceptable carrier. When administered at a daily dosage of between 0.05 mg to about 10,000 mg of active ingredient per unit dose, the substance can be used to treat various disorders of a nervous system such as pain, insomnia, anxiety, neurosis, depression, as well as withdrawal symptoms experienced by drug addiction patients, especially for patients addicted to opiate-based drugs. The substance can be delivered in a number of ways of systemic administration of a pharmaceutical agent including oral, parenteral, transdermal, and transmucosal administration. One disclosed method of administration involves a subcutaneous implant providing a continuous release of an active ingredient at an effective daily rate over the entire treatment period ranging from 5 to 30 days, and preferably from 13 to 20 days.

18 Claims, 2 Drawing Sheets

SUBSTANCE WITH SEDATIVE EFFECT

CROSS-REFERENCE DATA

This application claims foreign priority benefits of a Russian Patent Application No. 2002107079/14 filed 19 Mar. 2002, This application is a continuation-in-part of the U.S. patent application Ser. No. 10/389,538 filed Mar. 14, 2003, now U.S. Pat. No. 7,087,640. This application is a continuing application from the U.S. patent application Ser. No. 11/459,659 filed Jul. 25, 2006, now abandoned. All three cited patent applications have the same title as the present application and are incorporated herein in their entirety by reference.

BACKGROUND OF THE INVENTION

The present invention relates generally to pharmaceutical compounds and methods for the treatment of disorders relating to the nervous system in animals and humans. More specifically, the invention relates to the use of a subset of gamma-pyrones in pharmaceutically acceptable forms for the treatment of various disorders relating to the peripheral and central nervous system. For the purposes of this description, the terms "disorders relating to the nervous system" or "neurotic disorders" include among others such conditions as pain, depression, anxiety, insomnia, neurosis, etc., as well as pain and other symptoms associated with the abstinence syndrome experienced by chemical and drug abuse patients. All of these conditions involve the neurons of the nervous system.

Sedative compounds known in the art are a chemically varied group of compositions of natural and synthetic origin that predominantly have a tranquilizing effect on the central nervous system. Different sedatives produce different physiological effects. Understanding of these effects is helpful in selectively treating various disorders. This mechanism of action is not always entirely clear but it is believed that sedative drugs in general are intended to cause selective suppression of subcortical (limbus) and cortical brain structures, which regulate emotions.

The mildest examples of sedative drugs include extracts of motherwort, passiflora, valerian root (Tinctura Valeriana), bromides of caustic metals (Kalium bromatum, Natrium bromatum). These drugs typically cause only a light tranquilizing effect on the subject. Stronger tranquilizers are used to lower a patient's anxiety. These are synthetic medicinal preparations, examples of which include derivatives of benzodiazepin (diazepam), diphenyl methane (benactyzine), propanediol (mepropan) and trioxazin.

Hypnotic compounds (Phenobarbital for example) in small doses are also used as sedative drugs along with various neuroleptic agents (aminazine, tisercin) and some other compounds. Examples of such additional compounds include Bekhterev's mixture (sodium bromide, lychnis infusion, codeine phosphate), Corvalolum (ethyl ether of α-bromine isovaleric acid, monosodium salt of Phenobarbital, mint oil, ethyl alcohol, water), and Validol (menthol solution in menthyl valerate).

An example of a general sedative compound is shown in the U.S. Pat. No. 5,506,268 by Balandrin describing the use of isovaleramide as a mild anxiolytic and sedative agent.

The side effects of these medicinal preparations are a reduced ability to concentrate, drowsiness, and lower mental and physical effectiveness. In addition, patients often become dependent on a sedative in the course of treatment, reducing the desired effect, and a replacement sedative is needed to maintain the desired effect.

The need therefore exists for new sedative compounds that do not cause these side effects or drug dependency.

Pain is an unpleasant sensory and emotional experience associated with actual or potential tissue damage. In considering approaches to the treatment of pain, it is important to understand the distinction between acute and persistent or chronic pain. Acute pain occurs as a result of tissue injury, and is mediated by chemical, mechanical or thermal stimulation of pain receptors known as nociceptors. Acute pain serves a protective function, conditioning avoidance behavior of situations and events leading to such potential tissue damage.

In contrast to acute pain, chronic or persistent pain in itself constitutes a disease which serves no protective biological function. Chronic pain is unrelenting and can persist for years and frequently cannot be associated with a single or specific injury. Chronic pain predominantly constitutes chronic inflammatory pain (e.g. arthritis) or "neuropathic pain", which can be defined as pain initiated or caused by a primary lesion or dysfunction within the nervous system (Mersky and Bogduk, Classifications of Chronic Pain, 2nd edition. Seattle IASP Press: 394, 1994, De Andres and Garcia-Ribas, Pain Practice 3: 1-7, 2003). Neuropathic pain is associated with a variety of disease states and present in clinical settings for patients with a wide range of symptoms. (Woolf and Mannion Lancet 353: 1959-64, 1999). It does not require specific pain receptor stimulation although such stimulation can add to the intensity of the pain sensation (Baron Clinical J. Pain 16 (suppl2):512-520, 2003).

Neuropathic pain is often reported as having a lancinating or continuous burning character and is frequently associated with the appearance of abnormal sensory signs such as allodynia and hyperalgesia. Alloydnia is defined as pain resulting from a stimulus that does not normally elicit a painful response, and hyperalgesia is characterized by an increased pain response to normally non-painful stimuli. Some disorders characterized by neuropathic pain include mono-radiculopathies, trigeminal neuralgia, post-herpetic neuralgia, phantom limb pain, complex regional pain syndromes, back pain and the various peripheral neuropathies. Neuropathic pain may also be associated with diabetes, multiple sclerosis, radio- or chemotherapy and infections such as HIV and tuberculosis. Neuropathic pain may also result as a side effect of drug treatment or abuse.

For clinical purposes, nociceptive pain can be classified as somatic or visceral. Somatic pain results from prolonged activation of nociceptive receptors in somatic tissues such as a bone, joint, muscle or skin. Visceral pain, on the other hand, manifests from activation of nociceptive receptors by pathological mechanisms such as mechanical injury, x-ray irradiation, toxic agents, etc.

Neuropathic pain can be characterized by the following clinical features (Teng and Mekhail, Pain Practice, 3: 8-12, 2003, Rajbhandari et al, Pain, 83: 627-629, 1999, Melzack et al, Ann NY Acad Sci, 933: 157-174, 2001):

1. There is the presence of an abnormal, unpleasant sensation (dysesthesia) that frequently has a burning or electrical quality with an occasional paroxysmal, brief, shooting, or stabbing quality;
2. Although the onset of most neuropathic pain is within days after the precipitating injury, there is no absolute temporal relationship to the originating neural trauma such that it can begin weeks, months, or even years later;
3. Pain may be felt in a region of sensory deficit;
4. Non-noxious stimuli may be painful (allodynia);
5. Noxious stimuli may produce greater than normal response (hyperalgesia);

6. There may be an increase in the intensity of pain with repeated stimuli and the pain may persist after the removal of stimuli.

Although there are numerous available therapies for acute pain caused by stimulation of the nociceptors, especially treatment with opioid and non-steroidal anti-inflammatory drugs (NSAIDs), neuropathic pain is an area of largely unmet therapeutic need. Due to the distinct patho-physiochemical mechanisms and clinical manifestations associated with neuropathic pain relative to pain caused as a result of nociceptor stimulation or acute pain, agents useful in the treatment of pain caused as a result of nociceptor stimulation or acute pain have reduced effectiveness in neuropathic pain treatment.

There are basically two kinds of analgesics: non-narcotics and narcotics. It should be noted that some references include aspirin and other non-steroidal anti-inflammatory drugs (NSAIDS) in the class of analgesics, because they have some analgesic properties. Aspirin and NSAIDS primarily have an anti-inflammatory effect, as opposed to being solely analgesic.

Acetaminophen (a NSAIDS) is the most commonly used over-the-counter, non-narcotic analgesic. Acetaminophen is a popular pain-reliever because it is both effective for mild to moderate pain relief and relatively inexpensive. It must be emphasized though that the safety of acetaminophen is tied to proper use of the drug (use according to specific prescribing instructions). If acetaminophen is not used according to the directions on the label, serious side effects and possible fatal consequences can occur. For example, taking more than 4000 mg/day, or using it long-term, can increase the risk of liver damage. The risk of liver damage with acetaminophen use is also increased by ingesting alcohol. Many people do not realize that acetaminophen is found in more than 600 over-the-counter drugs. It can be found in combination with other active ingredients in many cold, sinus, and cough medications. The cumulative effect of acetaminophen must be considered if one is taking multiple drugs which contain acetaminophen. In the body, acetaminophen changes into metabolites which are eliminated from the body, and by taking more than the recommended maximum daily dose of acetaminophen, more toxic metabolites are produced than can be eliminated, resulting in liver damage.

There are two types of narcotic analgesics: opiates and opioids (derivatives of opiates). Opiates are the alkaloids found in opium (a white liquid extract of unripe seeds of the poppy plant). Opioids are any medications which bind to opioid receptors in the central nervous system or gastrointestinal tract. There are four broad classes of opiates/opioids:

1. Endogenous opioid peptides (produced in the body: endorphins, dynorphins, enkephalins);
2. Opium alkaloids (such as morphine, codeine, thebaine);
3. Semi-synthetic opioids (such as heroin, oxycodone, hydrocodone, dihydrocodeine, hydromorphone, oxymorphone, nicomorphine); and
4. Fully synthetic opioids (such as pethidine or Demerol, methadone, fentanyl, propoxyphene, pentazocine, buprenorphine, butorphanol, tramadol, and more).

Opiates and opioids are used in medicine as strong analgesics, for relief of severe or chronic pain. Interestingly, there is no upper limit for the dosage of opiates and opioids used to achieve pain relief, but the dose must be increased gradually to allow for the development of tolerance to adverse effects (for example, respiratory depression). According to eMedicine, "Some people with intense pain get such high doses that the same dose would be fatal if taken by someone who was not suffering from pain."

There have been debates over the addictive potential of opiates and opioids vs. the benefit of their analgesic properties for treating non-malignant chronic pain, such as chronic arthritis. Some experts believe opiates and opioids can be taken safely for years with minimal risk of addiction or toxic side effects. The enhanced quality of life which opiates and opioids may provide the patient must be considered. Common side effects of opiates and opioids are nausea, vomiting, drowsiness, dry mouth, miosis (contraction of the pupil), orthostatic hypotension (blood pressure lowers upon sudden standing), urinary retention and constipation. Less common side effects noted are confusion, delirium, hallucinations, hives, itch, hypothermia, bradycardia (slow heart rate), tachycardia (rapid heart rate), raised intracranial pressure, uretic or bilary spasms, muscle rigidity and flushing. The most severe side effects are respiratory depression and a fatal overdose.

In particular, the effectiveness of opiates and opioids in the treatment of neuropathic pain is diminished relative to their use in the treatment of pain caused as a result of nociceptor stimulation or acute pain, and drug dose response curves for treatment of neuropathic pain are shifted to the right of those for treatment of pain caused as a result of nociceptor stimulation or acute pain (Teng and Mekhail, 2003 supra, De Andres and Garcia-Ribas, 2003 supra, Stuteet al J. Pain Symptom Management 25: 1123-1131, 2003).

As reported by Salynn Boyles in WebMD Medical News on Mar. 26, 2003 in an article entitled, *Morphine-Like Drug Cuts Neuropathic Pain, but Risks Still Unknown*, researchers found that high-dose treatment with opioids provided much greater chronic pain relief than lower doses of the drug. Pain was reduced by 36% among patients in the high-dose group, compared with 21% in those taking lower doses. "When you have pain you aren't looking for a 20% or 30% drop in that pain," the McGill University professor told WebMD. "The objective is to have no pain, and very few patients experience complete pain relief with the available treatments."

Due to the diminishing effects over time (tolerance) of opioids in subjects suffering from neuropathic pain, the use of opioids is often frequent and sustained. This over use is often associated with addiction, the development of tolerance and an increase in the number and severity of side effects associated with opioid use.

A pharmacological mainstay of the conventional clinical management of neuropathic pain are tricyclic anti-depressants and certain anti-convulsants, but even these achieve a reduction in pain of less than 50% in greater than 50% of patients treated. These agents are also associated with significant side effect profiles.

There is a pressing need therefore for improved regimes for the treatment of neuropathic and inflammatory pain as well as improved regimes for treating disease conditions which have a neuropathic or inflammatory pain component.

Pharmaceutical compounds used in treating patients with chemical and drug abuse define an important sub-category in the general area of drugs. It is common knowledge that there are many individuals who become addicted to certain types of drugs taken either for medical reasons or for "recreational", non-medical use. Addiction, as has been defined by the Drug Addiction Committee of the National Research Council, is a state of periodic or chronic intoxication detrimental to the individual and produced by the repeated administration of a drug. Thus, an "addictive drug" as used herein is one that is initially used for any one of a number of purposes, e.g., for the relief of physical or psychic pain, and which if used consistently leads to dependency on the part of the individual taking the drug. The addicted individual develops a continuing craving (physical and psychological) for the drug and experiences "withdrawal symptoms" if an attempt is made to discontinue drug use. The terms "withdrawal syndrome" and "abstinence syndrome" are used to mean the same condition of the patient for the purposes of this description.

Various pharmacological approaches for treating drug dependence have been tried. These approaches have typically involved attempts at treating the physical craving for the abused drug or alleviating the physical symptoms associated withdrawal. The following references relate to some known methods and compositions for treating drug addiction and/or symptoms of withdrawal from drug dependency. U.S. Pat. No. 4,786,653 by Golwyn relates to the administration of phenelzine or an equivalent phenylalkylhydrazine, substances that are physiologically incompatible with addictive drugs such as amphetamines and cocaine. U.S. Pat. Nos. 1,796,977 and 1,782,111 describe the preparation of disulfuram ("Antabuse"), an alcohol deterrent. U.S. Pat. No. 4,696,818 by Kim relates to a method for alleviating symptoms associated with a variety of drugs, the method comprising administering an herbal composition to the drug dependent individual. U.S. Pat. No. 3,706,831 by Plotnikoff also describes a method for treating addiction to any one of a number of different types of drugs, which method involves administering to the addict a composition containing 2-imino-5-phenyl-4-oxazolidinone. U.S. Pat. Nos. 4,117,161 and 4,124,715 by Pozuelo disclose methods and compositions for treating withdrawal from narcotics and amphetamines which involve administration of alphamethyl-para-tyrosine or fusaric acid to the affected individual.

Treatment of nicotine withdrawal is described in the U.S. Pat. No. 4,325,952 by Baiocchi et al. and involves the use of a piperazine compound to treat the symptoms associated withdrawal from nicotine. U.S. Pat. No. 4,788,189 by Glazer involves treatment of nicotine withdrawal by administration of clonidine in conjunction with a tricyclic antidepressant drug. U.S. Pat. No. 4,276,890 by Fichera describes a composition for alleviating symptoms of nicotine withdrawal by administering to the affected individual a composition containing a gamma-pyrone such as maltol or ethyl maltol.

Opiates and their numerous forms, including opium, codeine, morphine, heroin, etc. as well as its other alkaloids and including synthetic or derived substitutes, constitute a large segment of narcotics in general. Their use has become more widespread recently, in both the "recreational drug" and pharmaceutical segments. The primary method of treatment for dependence on narcotics is the discontinuation of narcotics and minimization of the abstinence syndrome. Officially permitted methods of the discontinuation of narcotics involve the replacement of the offending drug from the opioid receptors and their substitution by one of three possible types of ligands:

1. Antagonists of opioid receptors such as naltrexone, naloxone, nalmephine, and antaxone;
2. Agonists/antagonists such as pentazocine, butorphanol, nalbuphine, and buprenorphine aimed to activate receptors of a particular subtype such as kappa, while blocking receptors of another subtype such as mu; and
3. Agonists such as methadone and others that are better controlled and have a lower affinity to receptors, this method is called substitution therapy.

Each of these approaches has its own disadvantages. In the case of antagonists, there is no relief from the pain and other symptoms of withdrawal syndrome. The most severe, long-lasting manifestations of withdrawal syndrome cannot be eliminated either by initial general narcosis or with the assistance of anesthetics, tranquilizers, neuroleptics or antidepressants. These substances have numerous side effects while the incidence of relapse is rather high. With the use of agonists, the withdrawal syndrome is less pronounced; however, a dependence often develops on the medication that is also, in fact, a narcotic, although with a lower affinity to opioid receptors than, for instance, morphine or heroin. Besides, the duration of such substitution therapy is rather long, up to 3-6 months and more. Due to their psychological instability, drug addicts often "change their mind" and refuse treatment.

Therefore, a very substantial need exists for a therapeutic method of treating drug abuse such that a drug-addicted individual is readily able to discontinue use of an abused drug without encountering the above-mentioned problems and withdrawal symptoms.

SUMMARY OF THE INVENTION

Accordingly, it is an object of the present invention to overcome these and other drawbacks of the prior art by providing a novel group of compounds and compositions and therapeutic methods for causing a sedative effect without the side effects of other known sedatives.

Its is also an object of the present invention to provide a novel group of compositions and administration methods for a longer lasting sedative and pain relief effect as compared with known pharmacological compounds.

It is another object of the present invention to provide a novel group of pharmaceutically acceptable compositions and a method of administration thereof capable of producing a ligand-receptor binding. More specifically, the object of the invention is to provide a novel group of compositions and a method of their administration causing the activation of a signaling pathway that involves an opioid (or opioid-like) receptor but without causing a drug dependency of its own.

It is a further object of the present invention to provide a novel group of pharmaceutically acceptable compositions and methods of administration thereof for treatment of chemical and narcotics abuse.

It is yet a further object of the present invention to provide a novel group of pharmaceutically acceptable compositions and a method of administration thereof for treatment of patients addicted to opiates and opioids in all of their various natural and synthetic forms.

The compositions and methods of the invention are based on a better understanding of the physiological role of a recently discovered cell membrane signaling mechanism, including receptors located in the opioid receptor area (opioid or "opioid-like" receptors) and the tetrodotoxin-resistant slow sodium channel known as $Na_v1.8$. Several compounds chosen from the group of gamma-pyrones have been used to activate this cell membrane signaling mechanism, the necessary molecular configuration for producing such effect has been established and the novel subset of such active gamma-pyrones compounds has been determined. These substances have their effect because the active centers of the gamma-pyrone molecule-agonist (in salt form) are located at a similar distance from each other as the active atoms of morphine.

One of the preferred compounds of the invention is comenic acid, also known as 5-hydroxy-4-oxo-4H-pyran-2-carbon acid, as well as 5-hydroxy-gamma-pyrone-2-carboxylic acid. It has been discovered that administration of this acid to animals at a specified dosage produces a desired sedative effect without causing drug dependency after a 50-day period of continued daily use. The effect is long lasting, up to 24 hours after administration. The effective dosage range was found to be from about 0.005 to about 200 milligrams of comenic acid per 1 kilogram of body weight of the subject. The acid can be administered in a number of pharmaceutically acceptable ways by mixing it with known and biologically acceptable carriers. Administration methods include all parenteral modes, including injection (intravenously, subcutaneously, intramuscularly or intraperitoneal), transdermally, transmucosally, etc. It was discovered that over a relatively short period of time, administration of comenic acid in a pharmacologically effective dose as described herein provides an effective treatment for the cure of narcotic dependency in animals, and that the effective duration of administration ranges from about 5 to about 30 days with a preferred duration from about 13 to about 20 days. This duration compares quite favorably to a typical drug abuse treatment cycle of 3 to 6 months using substitution methods such as methadone.

Another preferred compound of the invention is 5-methoxy-gamma-pyrone-2-carboxylic acid. Based on patch clamp experiments on dorsal root ganglion neurons, it has been found that 5-methoxy-gamma-pyrone-2-carboxylic acid has similar effect as comenic acid on the $Na_v1.8$ slow sodium channel, though less strongly exhibited. 5-methoxy-gamma-pyrone-2-carboxylic acid exists in the form of white or yellowish crystals, has a melting point of 282° C., and has a molecular mass equal to 170.122 ($C_7H_6O_5$). 5-methoxy-gamma-pyrone-2-carboxylic acid is moderately water- and alcohol-soluble (though somewhat less so than comenic acid) and practically insoluble in non-polar organic solvents. 5-methoxy-gamma-pyrone-2-carboxylic acid can be produced using kojic acid with good yield.

Other compounds from the gamma-pyrone class of compounds can also be used. The subset of gamma-pyrones that are active in modulating the $Na_v1.8$ slow sodium channel is hereinafter defined based on the geometry of the molecule and the distance between its active points (when such molecule is in salt form). Other specific examples of compounds usable for the purposes of this invention, including meconic acid, are described in more detail below.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A treatment for causing sedation and for reducing pain, anxiety and depression was discovered about 100 years ago. Morphine is one of the approximately 20 alkaloids present in natural opium. It is the best known agonist of opioid receptors and triggers a sequence of intracellular signaling processes.

The first step in this sequence is ligand-receptor binding, in which the target of morphine is a well-studied class of cell membrane receptors (opioid receptors). Activation by morphine of opioid receptors, which are linked to ion channels, can produce analgesic and sedative effects. Opioids decrease pain sensitivity by reducing the calcium-dependent release of neuromediators from presynaptic terminals, thus inhibiting signal transmission between neurons. It has been recently published by one of the inventors of the present invention that there exists a previously unknown interaction between the opioid (or "opioid like") receptor, $Na^+$, $K^+$-ATPase and the activation gating system of $TTX_r$, sodium channels (see B. V. Krylov et. al., Russian Journal of Physiology, Vol. 85, No. 2, pages 225-236, 1999. English translation of the title: *Morphine Decreases the Voltage Sensitivity of Slow Sodium Channels, Neuroscience and Behavioral Physiology*, Vol. 30, No. 4, 2000, pages 431-439). Therefore, there exists a newly discovered signaling pathway in the cell membrane of a sensory neuron (dorsal root ganglion cell).

The principle behind the present invention is to substitute morphine with a more friendly and benign compound, which is still capable of activating this newly-discovered signaling pathway, thereby reducing pain and pain and other negative effects of the abstinence syndrome, but does not create the physical dependency or euphoria associated with morphine and other opiate alkaloids and their derivatives.

Gamma-pyrones are generally known to be used for medicinal purposes. They have been predominately used as food additives, viral agents (as described for example in the PCT publication No. WO 92/13850); for treatment of iron-deficiency anemia (see for example the U.S. Pat. No. 4,575, 502); high blood sugar and diabetes (see for example U.S. Pat. No. 5,888,993), allergic conditions (see for example U.S. Pat. No. 4,198,426), and other ailments. They have never been suggested to be used for sedation, pain relief or drug abuse related pain relief since there was no rationale known for doing so.

Comenic acid was found to be an excellent representative of the gamma-pyrone group in use for the purposes of the present invention. 5-hydroxy-4-oxo-4H-pyran-2-carbon acid, or comenic acid, exists in the form of yellowish crystals, has a melting point of about 270° C., and has a molecular mass equal to 156.095 ($C_6H_4O_5$). Comenic acid is moderately water- and alcohol-soluble and practically insoluble in nonpolar organic solvents. Comenic acid is produced from kojic acid with good yield. Comenic acid is one of the ingredients of a widely used antibacterial medicinal preparation sold in Russia, Baliz-2.

To demonstrate its sedative effect, comenic acid was compared to Valerian extract. The sedative effect was measured by the change in motor activity of male rats of Wistar line with the mass of 0.20-0.23 kg in "the open field" test [Guiding and Method Materials in Experimental and Clinical Study of New Drugs. Part 2. M., 1980, pp. 126-133]. The results of the tests are presented in the table 1 below.

Group 1—Control.

Male rats were subjected to the enteral introduction of 0.5 ml of saline solution. Then, the animals were divided into two groups. The rats in the first group were tested in "the open field" 60 minutes after the solution's introduction. The rats in the second group were tested 90 minutes after the introduction. The test consisted of the rat being placed in the center of "the open field", and then the number of squares of "the open field" that the rat crosses within 5 minutes is counted (an estimation of motor activity).

Groups 2-5—Valerian Extract.

Valerian extract was steamed until it became dry. Then, the dry remains were dissolved in saline in the required dosage (see table 1 and rated in mg/kg of a rat's body weight). The solution obtained was introduced into rats in the same way as for control. The testing of rats in "the open field" was also carried out as described for control.

Groups 6-9—Comenic Acid.

Comenic acid was dissolved in saline in the desired dosages (see table 1 below). The solution's pH was adjusted to equal 6.5-6.8 using concentrated NaOH solution. Comenic acid was introduced into the rats in the same way as in control. The testing of rats in "the open field" was carried out as described for control group as well.

TABLE 1

INFLUENCE OF COMENIC ACID ON RATS' MOTOR ACTIVITY IN "THE OPEN FIELD" TEST

| No. | Experiment conditions | Dosage of medicinal preparation (mg/kg of body weight) | Motor activity after the preparation's introduction (n) | | Lowering motor activity relative to the control (%) | | Lowering motor activity relative to the Valerian extract (%) | |
|---|---|---|---|---|---|---|---|---|
| | | | 60 min | 90 min | 60 min | 90 min | 60 min | 90 min |
| 1 | Saline | 0 | 50.3 ± 7.8 | 47.5 ± 8.2 | | | | |
| 2 | Valerian | 1 | 53.9 ± 8.1 | | −7 | 11 | | |
| 3 | extract | 10 | 48.5 ± 10.2 | | 4 | 20 | | |
| 4 | | 50 | 38.9 ± 9.8 | | 23 | 38 | | |
| 5 | | 100 | 40.8 ± 4.5 | 38.1 ± 10.5 | 19 | 54 | | |
| | | | | 31.5 ± 5.8 | | | | |
| | | | | 21.8 ± 8.1 | | | | |
| 6 | Comenic | 1 | 43.9 ± 6.8 | 51.2 ± 8.3 | 13 | −8 | 19 | −21 |
| 7 | acid | 10 | 37.6 ± 5.9 | 41.6 ± 6.8 | 25 | 12.5 | 22 | −9 |
| 8 | | 50 | 18.7 ± 3.3 | 15.2 ± 3.1 | 63 | 68 | 52 | 52 |
| 9 | | 100 | 13.4 ± 4.8 | 10.3 ± 2.8 | 73 | 78 | 67 | 53 |

Results above indicate that the administration of comenic acid to Wistar male rats with a body weight of 200-230 g in dosage of 50 and 100 mg/kg of body weight has lowered their motor activity by 68% and 78%, respectively, as compared with the control group (saline), and 52 and 53%, respectively, as compared with the valerian extract. Therefore, the sedative effect of comenic acid was twice that of valerian extract in these experiments with rats.

These experiments were repeated with the same animals and resulted in good reproducibility of results. Also, there were no other side effects of the administration of comenic acid noticed. In addition, there was no development of tolerance to comenic acid developed by the rats and no indication of drug dependency.

Comenic acid (in medicinal form, referred to as "Anoceptin™") was also tested on rats with transplanted tumors (Pliss limphosarcoma) to determine if it stimulated tumor growth (Effect of medicine Anoceptin on the growth of transplantable tumor in rats, State Oncology Institute, 2006, Saint-Petersburg, Russia). Pliss limphosarcoma was transplanted subcutaneously into 20 rats. Forty-eight hours after transplantation, the rats were randomly assigned into groups (10 rats in experimental group, and 10 in control group) and the injections were started. Both groups were injected i.p. (intraperitoneal) once per day, 5 times per week and given a total of 10 injections each. The experimental group was administered 50 mg/kg of comenic acid in each injection, while the control group was injected with 1.5 ml of physiological solution. Comenic acid was utilized in its medicinal form ("Anoceptin™"), a 1% solution with ions of proper moiety. For both groups, the size of the tumor was measured on day 6, 9, 13 and 16 of the experiment, and the volumes were calculated. Based on the comparison between the two groups of 1) such tumor volumes and 2) rat mortality, it was determined that under the described conditions, comenic acid had no effect (no stimulation and no inhibition) on the growth of transplantable tumors of Pliss limphosarcoma. The data was determined to be statistically significant, with $p<0.05$.

Comenic acid (in medicinal form, referred to as "Anoceptin™") was also tested on rats with transplanted tumors (Ehrlich carcinoma) to determine if it stimulated tumor growth (Effect of medicine Anoceptin on the growth of transplantable tumor, State Oncology Institute, 2006, Saint-Petersburg, Russia). Ehrlich carcinoma was transplanted subcutaneously into 20 rats. Forty-eight hours after transplantation, the rats were randomly assigned into groups (10 rats in experimental group, and 10 in control group) and the injections were started. Both groups were injected i.p. (intraperitoneal) once per day, 5 times per week and given a total of 10 injections each. The experimental group was administered 50 mg/kg of comenic acid in each injection, while each in the control group was injected with 0.125 ml of physiological solution. Comenic acid was utilized in its medicinal form ("Anoceptin™"), a 1% solution with ions of proper moiety. For both groups, the size of the tumor was measured on day 13, 16, 20, 23, 27, 30, 37 and 44 of the experiment, and the volumes were calculated. Based on the comparison between the two groups of 1) such tumor volumes and 2) rat mortality, it was determined that under the described conditions, comenic acid had no effect (no stimulation and no inhibition) on the growth of transplantable tumors of Ehrlich carcinoma. The data was determined to be statistically significant, with $p<0.05$.

The results of extensive in vitro patch-clamp experiments and ab initio quantumchemical calculations indicate that not all gamma-pyrone compounds exhibit physiological activity on the $Na_v1.8$ slow sodium channel. Moreover, it was determined which functional groups should be present in gamma-pyrone molecules in order for these molecules to be capable of binding to the opioid (or opioid-like) receptor and activating the referenced newly discovered signaling pathway.

Figure 1:
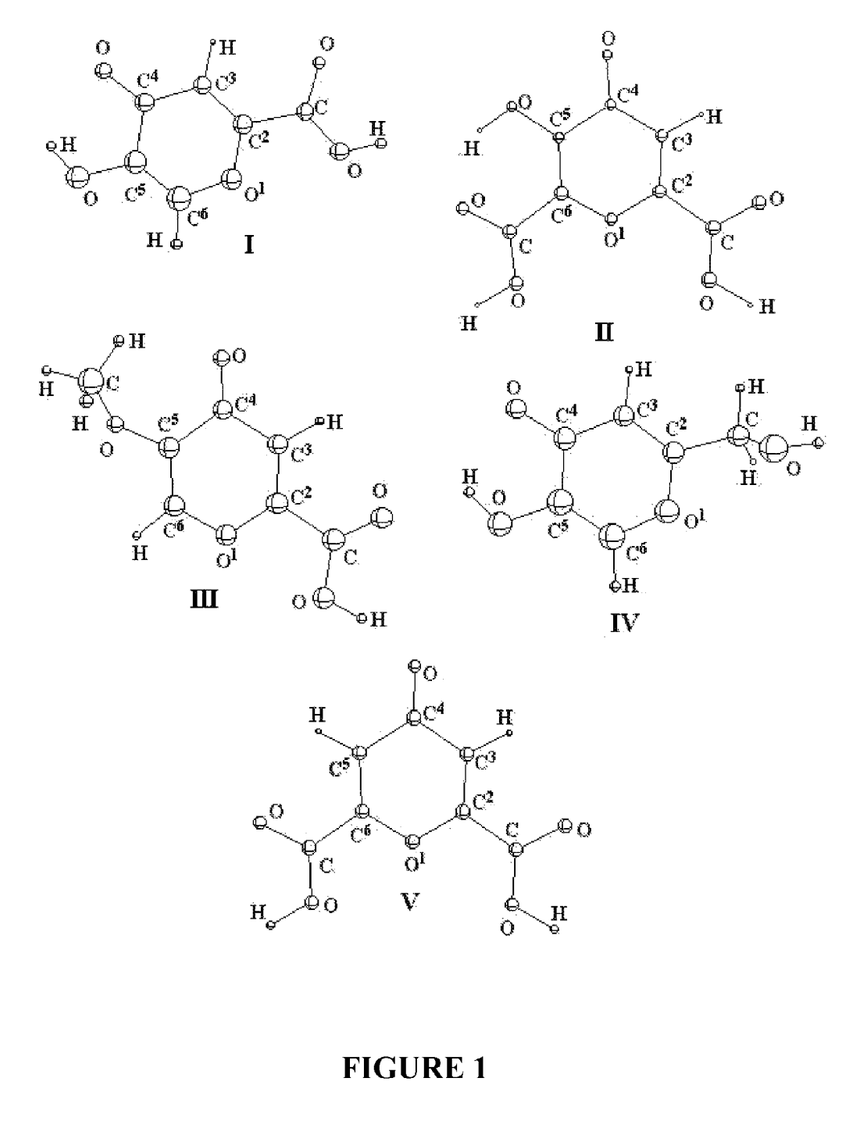
FIG. 1 is the spatial structures of gamma-pyrone derivatives in free acid form: (I) comenic acid (5-hydroxy-γ-pyrone-2-carboxylic acid), (II) meconic acid (3-hydroxy-γ-pyrone-2,6-dicarboxylic acid), (III) 5-methoxy-γ-pyrone-2-carboxylic acid, (IV)kojic acid (2-hydroxymethyl-5-hydroxy-γ-pyrone, and (V) chelidonic acid (γ-pyrone-2,6-dicarboxylic acid), and FIG. 2 is the spatial structures of gamma-pyrone derivatives in forms including the maximal number of bound cations: (I) comenic acid (5-hydroxy-γ-pyrone-2-carboxylic acid), (II) meconic acid (3-hydroxy-γ-pyrone-2,6-dicarboxylic acid), (III) 5-methoxy-γ-pyrone-2-carboxylic acid, (IV) kojic acid (2-hydroxymethyl-5-hydroxy-γ-pyrone), and (V) chelidonic acid (γ-pyrone-2,6-dicarboxylic acid).

The physiological effect on the $Na_v1.8$ channel of the following closely related gamma-pyrone derivatives (see FIG. 1) was investigated: I) comenic acid (5-hydroxy-gamma-pyrone-2-carboxylic acid), II) meconic acid (3-hydroxy-gamma-pyrone-2,6-dicarboxylic acid, III) 5-methoxy-gamma-pyrone-2-carboxylic acid, IV) kojic acid (2-hydroxymethyl-5-hydroxy-gamma-pyrone) and V) chelidonic acid (gamma-pyrone-2,6-dicarboxylic acid). Patch-clamp experiments determined that molecules I, II, and III modulated the activity of tetrodotoxin-resistant ($TTX_r$) $Na_v1.8$ slow sodium channels, whereas molecules IV and V did not exhibit such effect [Rogachevsky I. V., Plakhova V. B., Domnin I. N., Podzorova S. A., Krylov B. V. *Physiological role of gamma-pyrones*. Clinical Pathophysiology (Russian), in press]. Given that the modulating action on the $Na_v1.8$ channels of compounds I through III was totally blocked by nonspecific opioid receptor antagonist naltrexone, it was concluded that these compounds bind directly to an opioid (or opioid-like) receptor.

Ligands of opioid receptors normally have at least one positively charged moiety, which is generally thought to bind to an acidic residue of the receptor [Strader C. D., Fong T. M., Tota M. R. et al. *Structure and function of G-protein-coupled receptors*. Annual Review Biochemistry. 1994. V. 63, N 7. P. 101]. Modeling of various opioid receptors ($\mu$, $\delta$, $\kappa$) [Baldwin J. M., Schertler G. F. X., Unger V. M. *An alpha-carbon template for the transmembrane helices in the rhodopsin family of G-protein-coupled receptors*. J. Molecular Biology 1997. V. 272, N 1. P. 144; Pogozheva I. D., Lomize A. L., Mosberg H. I. *Opioid receptor three-dimensional structures from distance geometry calculations with hydrogen bonding constraints*. Biophysics J. 1998. V. 75, N 8. P. 612; Zhorov B. S., Ananthanarayanan V. S. *Homology models of µ-opioid receptor with organic and inorganic cations at conserved aspartates in the second and the third transmembrane domains*. Archives Biochemical Biophysiology. 2000. V. 375, N 1. P. 31] made it possible to construct a theoretical model to conform with the vast amount of experimental data on the affinities of diverse ligands, describing the structure-activity relationships in a series of closely related ligands, the influence of selective mutations on its functioning and the properties of opioid receptors. In particular, it was determined that two aspartate residues, absolutely conserved in all families of opioid receptors described to date, play an important role in ligand binding. It is highly probable that the opioid (or opioid-like) receptors which bind gamma-pyrones also contain these residues. None of the above compounds I-V possesses positively charged groups, which led to our assertion that gamma-pyrones bind to the receptor with the assistance of one or several inorganic cations.

Carboxy groups in the α-position to the pyranone ring oxygen can form salts with inorganic cations, whereas the hydroxy and the carbonyl groups in adjacent positions of the pyranone ring are known to chelate divalent cations in water and 50% aqueous dioxane [e.g., Bryant B. E., Fernelius W. C. *Some metal complexes of kojic acid*. J. American Chemistry Soc. 1954. V. 76. N 21. P. 5351; Petrola R. *Spectrophotometric study on the equilibrium of substituted 3-hydroxy-4H-pyran-4-ones with Zn(II) ions in aqueous solution*. Finn. Chemistry Letters 1985. Vol. 12. N 5. P. 219; Okáč A., Kolařík Z. *Potentiometrische untersuchung von komplexsalzen der kojisäure in wässrigen lösungen*. Coll. Czech. Chem. Comm. 1959. Vol. 24. N 1. P. 266].

In patch-clamp experiments, all agents were added to an extracellular solution containing $Na^+$, $Ca^{2+}$ and $Mg^{2+}$ at concentrations of 65 mM, 2 mM and 2 mM, respectively [Rogachevsky I. V., Plakhova V. B., Domnin I. N., Podzorova S. A., Krylov B. V. *Physiological role of gamma-pyrones*. Clinical Pathophysiology (Russian), in press]. Comenic and kojic acids were shown to form stable chelates with $Ca^{2+}$ and $Mg^{2+}$ in 1:1 stoichiometry, given that the cation concentrations were at least ten times higher than those of the chelating agents [Bryant B. E., Fernelius W. C. *Some metal complexes of kojic acid*. J. American. Chemistry Society 1954. V. 76. N 21. P. 5351; Okáč A., Kolařík Z. *Potentiometrische untersuchung von komplexsalzen der kojisäure in wässrigen lösungen*. Coll. Czech. Chem. Comm. 1959. Vol. 24. No 1. Page 266]. Monovalent cations at high concentrations did not significantly affect the stability constants of chelate complexes of said gamma-pyrone derivatives with $Ca^{2+}$ and $Mg^{2+}$.

It was also shown [Okáč A., Kolařík Z. *Potentiometrische untersuchung von komplexsalzen der kojisäure in wässrigen lösungen*. Coll. Czech. Chem. Comm. 1959. Vol. 24. N 1. P. 266] that $Ca^{2+}$ and $Mg^{2+}$ kojic acid chelates were almost equally stable in aqueous solutions, so either of the cations could form chelates in our patch-clamp experiments. Since the concentrations of $Ca^{2+}$ and $Mg^{2+}$ in the patch-clamp experiments were several orders of magnitude higher than those of compounds I-V, the chelate stoichiometry was assumed to be 1:1. It should be noted that the ionic composition of the solutions used in our in vitro experiments and, in particular, the ratio of $Ca^{2+}$ and $Mg^{2+}$ concentrations, were chosen so as to provide the maximal stability of the cell membranes of isolated neurons, so the solutions used were regarded as a model of in vivo physiological conditions. However, $Mg^{2+}$ is known to act as a nonspecific blocker of synaptic transduction, and this highly negative physiological effect is exhibited at quite low $Mg^{2+}$ concentrations, such as 3 mM [Andrianov G. N., Puyal J., Raymond J., Ventéo S., Demêmes D., Ryzhova I. V. *Immunocytochemical and pharmacological characterization of metabotropic glutamate receptors of the vestibular end organs in the frog*. Hear. Res. 2005. Vol. 204. N 1-2. P. 200]. In additional, it has been shown that low-energy conformations of $Ca^{2+}$ complexes of opioid ligands closely resemble the morphine-$Ca^{2+}$ complex [Zhorov B. S., Ananthanarayanan V. S. *Similarity of $Ca^{2+}$-bound conformations of morphine and Met-enkephalin: a computational study*. FEBS Letters 1994. V. 354. N 2. P. 131; Zhorov B. S., Ananthanarayanan V. S. *Conformational analysis of the $Ca^{2+}$-bound opioid peptides: implications for ligand-receptor interactions*. J. Biomolecular Structural Dynamics 1995. V. 13. N 1. P. 1]. This data suggests an important physiological role of $Ca^{2+}$ in the binding of opioid ligands to the receptor. It was thus presumed that $Ca^{2+}$ is the cation, which is involved in the in-vivo formation of a ternary complex between the ligand, $Ca^{2+}$ and said opioid (or opioid-like) receptor.

To investigate the possible involvement of inorganic cations in the ligand-receptor binding process, a full ab initio (6-31G*/RHF) geometry optimization of molecules I-V (see FIG. 1) was performed. The molecules were considered not only in the form of free acids and their anions, but also (whenever possible) their $Na^+$ and $Ca^{2+}$ salts, $Ca^{2+}$ chelates, as well as $Na^+$ and $Ca^{2+}$ salts of $Ca^{2+}$ chelates. Calculations showed that the spatial and electronic structures of molecules I through V were quite similar [Rogachevsky I. V., Plakhova V. B. *Quantumchemical study of the equilibrium geometry and electronic structure of several gamma-pyrone derivatives*. Russian J. General Chemistry, in press]. The minor differences found were attributed to the variations in origin of the pyrone ring substituents and in the intramolecular hydrogen bonding patterns. The geometry optimization was performed not only for isolated molecules, but also for those in solvated phase in the framework of the polarizable continuum model (PCM) with the dielectric constants $\in=78.3$ (model of aqueous solution) and $\in=10$ (model of receptor binding pocket). The PCM calculations did not indicate any significant structural changes upon solvation of molecules I-V and their derivatives. Quantumchemical calculations have also shown that the processes of $Ca^{2+}$ chelation and formation of $Ca^{2+}$ and $Na^+$ salts were energetically allowed, and no steric restraints for $Ca^{2+}$ chelation were found [Rogachevsky I. V., Plakhova V. B., Podzorova S. A., *Metal-bound forms of 4H-pyran-4-one derivatives modulate nociceptive responses of sensory neurons*. Book of Abstracts of Alexander von Humboldt Foundation Conference "Technologies of the 21$^{st}$ Century: biological, physical, informational and social aspects", St. Petersburg, Russia, Sep. 27-29, 2005, P. 77.].

The spatial and electronic structure of the carboxy group of chelidonic acid (V), as well as the structure of the hydroxy and the carbonyl groups of kojic acid (IV), do not substantially differ from those of the corresponding functional groups in molecules I-III. The energetic effects of the formation of $Na^+$ and $Ca^{2+}$ salts of chelidonic acid (V) and $Ca^{2+}$ chelation by kojic acid (IV) are similar to the energies of analogous processes in molecules I-III. However, the patch-clamp results demonstrated that molecules IV and V did not influence the functioning of the TTX, $Na_v1.8$ channels, whereas molecules I-III did.

It was concluded that the inability of chelidonic (V) and kojic (IV) acids to bind to said opioid-like receptor, and therefore the lack of physiological effect of these molecules, is due to their inability to interact with two inorganic cations simultaneously. Chelidonic acid (V) lacks the hydroxy group and cannot chelate $Ca^{2+}$, whereas kojic acid (IV) lacks the carboxy group and cannot form salts at physiological pH.

Figure 2:
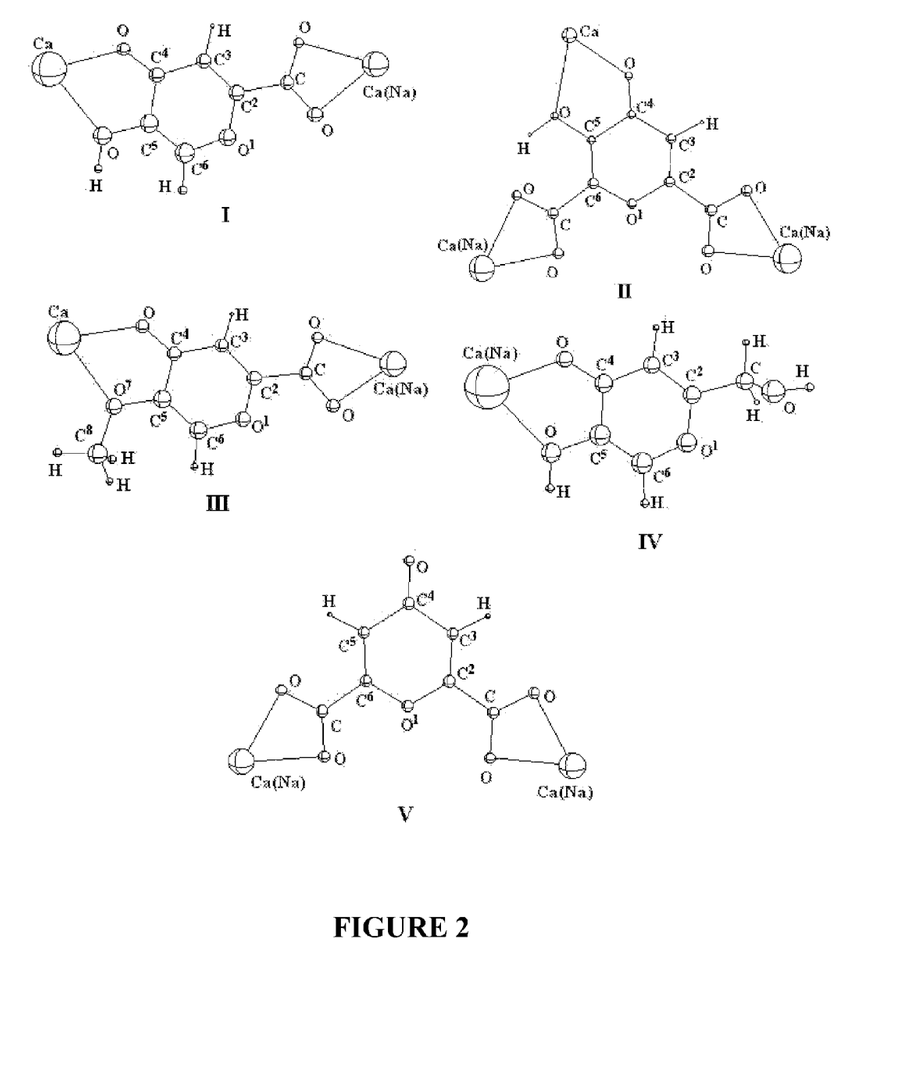

One explanation offered heretofore is that the active gamma-pyrone molecules I-III bind to the opioid-like receptor as the salt of $Ca^{2+}$ chelate (FIG. 2), interacting with conserved aspartates of the receptor during ligand binding. The chelated $Ca^{2+}$ forms a salt bridge with one of the aspartates, while the other aspartate interacts with the cation which serves as a counterion for the carboxy group of the ligand. The observed effect of gamma-pyrone molecule III accords with such mechanism of binding. As indicated by calculations, substitution of the hydroxyl for the methoxy group in position 5 of the pyrone ring does not impose any steric or energetic restrictions on $Ca^{2+}$ chelation [Rogachevsky I. V., Plakhova V. B., Podzorova S. A., *Metal-bound forms of 4H-pyran-4-one derivatives modulate nociceptive responses of sensory neurons*. Book of Abstracts of Alexander von Humboldt Foundation Conference "Technologies of the 21$^{st}$ century: biological, physical, informational and social aspects", St. Petersburg, Russia, Sep. 27-29, 2005, P. 77.].

In order for there to be complementarity between the gamma-pyrone molecules and the opioid (or opioid-like) receptor binding pocket, it is necessary that the distance between pyrone-bound cations match with the distance between the aspartates in the receptor. The intercationic distances in the salts of $Ca^{2+}$ chelates of molecules I-III were calculated to be between 9.4 Å and 9.6 Å, and did not depend significantly on the molecular structure of the ligands or origin of the cation ($Na^+$ or $Ca^{2+}$) forming salts with the carboxy group [Rogachevsky I. V., Plakhova V. B. *Quantum-chemical study of the equilibrium geometry and electronic structure of several gamma-pyrone derivatives*. Russian J. General Chemistry, in press]. According to the μ-opioid receptor model elaborated by Zhorov and Ananthanarayanan [Zhorov B. S., Ananthanarayanan V. S. *Homology models of μ-opioid receptor with organic and inorganic cations at conserved aspartates in the second and the third transmembrane domains*. Archive of Biochemical Biophysics 2000. V. 375, N 1. P. 31], there is likely a role for inorganic cations in ligand-receptor binding and receptor activation, and the distance between the aspartates of this type of receptor can vary in the range of 9-11 Å. It has been found that the intercationic distance in the complex of naloxone (a nonspecific opioid antagonist) associated with two $Na^+$ equals 8.4 Å, and the distance between cations in the complex of bremazocine (nonselective opioid agonist) with two $Na^+$ is 8.9 Å. Therefore, the intercationic distances of $Ca^{2+}$ chelate salts of molecules I-III are within the range of those distances obtained for (the similarly) metal-bound forms of μ-opioid agonists and antagonists.

Thus, according to the model of the mechanism of ligand receptor binding of said opioid (or opioid like) receptor, the prerequisites for gamma-pyrones receptor activity are 1) a carboxy group in position 2 of the pyranone ring, 2) a carbonyl group in position 4 of the pyranone ring, and 3) a substituent in position 5 which can participate in $Ca^{2+}$ chelation. Patch-clamp results demonstrated that the affinity of the test molecule to the receptor decreased in the following manner: II>I>III [Rogachevsky I. V., Plakhova V. B., Domnin I. N., Podzorova S. A., Krylov B. V. *Physiological role of gamma-pyrones*. Clinical Pathophysiology (Russian), in press].

Based on these observations, several conclusions concerning the potential effect of substituents in positions 3, 5 and 6 on the stability of ligand-receptor complex can be drawn. The presence of a carboxy group in position 6 (meconic acid, II) increases ligand affinity to the receptor as compared with comenic acid (I). It may be proposed that the carboxy group in position 6 is involved in additional interaction with one or several polar functional groups of the receptor by formation of intermolecular hydrogen or salt bonds. Based on this, introduction of a hydrophobic substituent in position 6 should reduce the affinity of gamma-pyrone derivatives to said opioid (or opioid-like) receptor. Given that both 5-methoxy-gamma-pyrone-2-carboxylic (III) and comenic (I) acids were shown to modulate the functioning of $TTX_r Na_v1.8$ channels, it is concluded that not solely a hydroxy group could be present in position 5. Other small functional groups possessing atoms with lone electron pairs (such as —OR or —NR$_2$), which may be involved in $Ca^{2+}$ chelation, could occupy this position 5. However, the decrease in activity of molecule III compared to molecule I indicates that the presence of a methoxy group instead of a hydroxyl in position 5 negatively affects the ability of gamma-pyrones to bind to the receptor. An increase in the size of the alkoxy group in position 5 will also lead to a further decrease or even total loss of physiological activity of the gamma-pyrone molecule. Bulky substituents in positions 3, 5 and 6 will decrease the affinity of gamma-pyrones to said receptor, since they will less readily be accommodated in the binding pocket.

Utility and Mode of Administration:

The present invention is useful as a sedative, pain reliever and for treating withdrawal symptoms from a wide range of drugs possessing addictive properties. The compositions of the invention are most useful in treating an individual withdrawing from narcotics, and more specifically from the use of opium alkaloids such as morphine, heroin and codeine, or from various synthetic variations thereof. The present invention also provides treatment for the depression, fear and anxiety experienced during withdrawal symptoms, and it is likely to provide improvements in such psychological pathologies commonly associated with patients experiencing chronic pain (neuropathic pain).

It is intended that the selected gamma-pyrones as described in the proceeding section be administered as a substitute for the abused drug. Typically, this will involve administration of a therapeutically effective amount of a composition containing the compounds of the invention at least once every twenty-four hours. By "therapeutically effective amount" is intended a dosage quantity effective to significantly alleviate physical craving for the drug of abuse as well as reducing the intensity of or eliminating other withdrawal symptoms associated with its discontinuance. Anxiety, depression, fear and other psychological pathologies associated with the withdrawal syndrome were reduced significantly in animal experiments. The effective daily dosage range was found to be from about 0.005 to about 200 milligrams of the compound per kilogram of body weight of the subject, providing a therapeutically effective blood level of the compound. The preferred dosage range is from about 0.05 to about 0.5 mg per kilogram of body weight per day. Such daily dosage can be achieved in a single application, multiple applications or using a continuous release application.

For use in human patients with an average weight ranging between 50 and 100 kg, the daily dosage entering the bloodstream is estimated to be from about 3 mg to about 100 mg per patient per day. It should of course be adjusted individually based on the decision of a treating physician and depending on the actual body weight of the patient, and depending on the mode of administration given that different modes result in varying losses in the amount of active ingredient actually transmitted into the blood stream. To allow for multiple applications per day ranging from 1 to 6, the active ingredient unit dosage range entering the bloodstream is estimated to be from about 1 mg to about 100 mg per application. In the preferred form, the unit dosage contains about 5 mg to about 20 mg of the active ingredient (daily dosage) mixed with a pharmaceutically acceptable carrier. Examples of such carriers were described in the parent patent application.

It was also found that daily administration of the compounds of the present invention to animals at a predetermined dosage produces a desired sedative and pain relief effect without causing drug dependency after 50 days of continued daily use. The effect from each administration lasts up to 24 hours.

For treating drug abuse patients, it is suggested that effective duration of treatment ranges from about 5 days to about 30 days. The most preferred duration is from about 13 to about 20 days.

For example, an optimal regimen for the parenteral (non-oral) administration will involve daily injection of an aqueous composition containing 5-20 mg of a gamma-pyrone compound as described above.

Administration of the compounds described herein can be via any of the accepted modes of systemic parenteral administration for therapeutic agents, including by injection, transdermal, transmucosal, subcutaneous implant, rectal, and other systemic modes. The preferred methods of administration are by injection, transdermal, transmucosal, and using a subcutaneous continuous release implant or with injected sorbents.

Parenteral administration is generally defined as non-oral administration, including by injection (intravenously, subcutaneously or intramuscularly), transdermally, transmucosally, etc. Preferably, in all administration modes, the gamma pyrone substance is combined with disassociated ions (preferably $Na^+$ and/or $Ca^{+2}$) of proper moiety, using for example sodium carbonate. Injectables can be prepared in conventional forms, either as liquid solutions or suspensions, solid forms suitable for solution or suspension in liquid prior to injection, or as emulsions. Suitable excipients include, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, or the like. The preferred method is to dissolve the gamma pyron substance in a biocompatible liquid along with disassociated ions (preferably $Na^+$ and/or $Ca^{+2}$) of proper moiety, using for example sodium carbonate.

A more recent approach for parenteral administration employs the implantation or injection of a slow-release or sustained-release system, such that an approximately constant level of dosage is maintained. See for example U.S. Pat. No. 3,710,795, the disclosure of which is incorporated by reference herein in its entirety. This application is especially beneficial in a subcutaneous continuous release form for drug addicts. In such case, a single visit to a physician can result in a subcutaneous implant of a slow release substrate (similar to nicotine withdrawal implant strips such as "Norplant") or an injected slow release sorbent impregnated with the active ingredient providing a constant therapeutically effective level of a compound of the invention over the entire treatment period as described above. Also, unauthorized removal of an implant to stop the therapy is much more difficult to do for a drug addict than to discontinue the medication delivered by other means.

The compounds of the invention may also be delivered through the body surface, i.e., transdermally or transmucosally. By "transdermal" as used herein is meant passage into and through the skin to achieve effective therapeutic blood levels. "Transmucosal" is intended to mean passage through a mucosal membrane of a living organism and thus includes delivery of drugs through nasal, lungs, sublingual, oral patch or buccal tissue. Transdermal or transmucosal delivery will involve topical application of the compounds of the invention in the form of an ointment, gel, cream, powder, spray, or the like, or may involve use of a drug delivery device as taught, for example, in U.S. Pat. Nos. 3,742,951, 3,797,494, or 4,568,343. Such compositions may optionally contain a permeation enhancer as known in the art, to increase the rate at which the compounds of the invention permeate through the skin or mucosal tissue.

Transmucosal administration of the present compositions is preferably effected transnasally, and more preferably by way of a nasal spray. Preferred vehicles for use in such a nasal spray are sterile saline solutions having a pH compatible with that of the nasal mucosa, and a particularly preferred vehicle for use herein is the nasal lubricant manufactured and sold under the trademark "Pretz" by Parnell Pharmaceuticals (San Rafael, Calif.), or a similar carrier.

Solid nasal powders or insufflations can also be used in a similar manner for transmucosal delivery. For such purpose, the compounds are administered in finely divided solid form together with a pharmaceutically accepted solid carrier. An example of such carrier is a finely divided polyethylene glycol ("Carbowax 1540") or finely divided lactose. Such compositions may also include other finely divided excipients.

For administering the compounds of the invention by inhalation of aerosol, the active ingredient compound is dissolved in a biocompatible liquid such as water, saline, or ethanol and mixed with a volatile propellant, for example dichlorotetrafluoroethane and dichlorodifluoromethane, and placed in a pressurized container preferably having a metering valve to release a predetermined amount of material based on the guidelines described above.

For solid compositions, e.g., for oral administration, the compounds will be formulated with pharmaceutical grades of acceptable carrier such as mannitol, lactose, starch, magnesium stearate, sodium saccharin, talc, cellulose, glucose, sucrose, magnesium carbonate, sodium carbonate, or the like. The compositions may also be formulated as suppositories using, for example, polyalkylene glycols (e.g., propylene glycol) as the carrier. Liquid pharmaceutically administerable compositions can be prepared by dissolving, suspending, dispersing, etc., the gamma-pyrones as described above and optional pharmaceutical carriers in an acceptable solution such as, for example, water, saline, aqueous dextrose, glycerol, ethanol, or the like, to thereby form a sterile and pyrogen-free solution or suspension. If desired, the pharmaceutical composition to be administered may also contain minor amounts of nontoxic auxiliary substances such as wetting or emulsifying agents, pH buffering agents or the like, e.g., sodium acetate, sorbitan monolaurate, triethanolamine sodium acetate, sodium carbonate, triethanolamine oleate, etc. Actual methods of preparing such dosage forms are known in the art, or will be apparent, to those skilled in the art; for example, see Remington's Pharmaceutical Sciences, Mack Publishing Co., Easton, Pa.

For oral administration, specifically, a pharmaceutically acceptable non-toxic composition is generally formed by the incorporation of any of the normally employed compounds described above. Such compositions can take the form of solutions, suspensions, tablets, pills, capsules, powders, sustained release formulations and the like. Such compositions can contain between about 1 wt. % to about 95 wt. % of the active ingredients, preferably between about 1 wt. % to about 70 wt. %.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for treatment of pain in a subject in need thereof comprising a step of modulating a slow sodium channel signaling pathway involving ligand-receptor binding in the opioid or opioid-like receptor site area and a tetrodotoxin-resistant slow sodium channel known as NaV1.8, wherein said step is performed by in-vivo administration of a substance comprising a pharmaceutically acceptable carrier and a gamma-pyrone, said gamma-pyrone having a molecule with a carboxy group in position 2 of the pyranone ring and a carbonyl group in position 4 of the pyranone ring, said gamma-pyrone molecule further having a substituent in position 5 capable of participating in Ca2+ chelation, said substance is administered in a dosage containing from about 0.05 mg to about 100 mg of said gamma-pyrone.

2. The method as in claim 1, wherein said gamma-pyrone is selected from a group consisting of comenic acid, meconic acid, and 5-methoxy-gamma-pyrone-2-carboxylic acid.

3. The method as in claim 1, wherein said in-vivo administration includes a daily dosage of said gamma-pyrone ranging from about 0.001 mg to about 1 mg per kilogram of body weight of said subject.

4. The method as in claim 1, wherein said in-vivo administration includes a daily dosage of said gamma-pyrone ranging from about 3 mg to about 100 mg.

5. The method as in claim 1, wherein said pain is associated with withdrawal syndrome in drug abuse treatment.

6. The method as in claim 5, wherein said drug is based on an opioid or its alkaloids.

7. The method as in claim 1, wherein the duration of said treatment is from about 5 to about 30 days.

8. The method as in claim 7, wherein said duration is from about 13 to about 20 days.

9. The method as in claim 1, wherein said substance is in a form suitable for parenteral administration.

10. The method as in claim 1, wherein said substance is in a form suitable for transmucosal administration.

11. The method as in claim 1, wherein said substance is in a form suitable for transdermal administration.

12. The method as in claim 1, wherein said substance is in a form suitable for epicutaneous administration.

13. The method as in claim 1, wherein said substance is in a form suitable for enteral administration.

14. The method as in claim 1, wherein said substance is in a form suitable for continuous release administration via an injection or a subcutaneous implant.

15. The method as in claim 14, wherein said substance is in a form for continuous release administration for the entire treatment duration.

16. The method as in claim 15, wherein said duration is between about 10 and about 30 days.

17. The method as in claim 1, wherein said pharmaceutically acceptable carrier includes disassociated ions of calcium.

18. The method as in claim 1, wherein said pharmaceutically acceptable carrier includes disassociated ions of sodium.

* * * * *